(12) United States Patent
Nagata et al.

(10) Patent No.: US 8,673,360 B2
(45) Date of Patent: Mar. 18, 2014

(54) COMPOSITIONS THAT ENABLE RAPID-ACTING AND HIGHLY ABSORPTIVE INTRANASAL ADMINISTRATION

(75) Inventors: Ryoichi Nagata, Kagoshima (JP); Shunji Haruta, Kagoshima (JP)

(73) Assignee: Shin Nippon Biomedical Laboratories, Ltd., Kagoshima (JP)

(*) Notice: Subject to any disclaimer, the term of this patent is extended or adjusted under 35 U.S.C. 154(b) by 792 days.

(21) Appl. No.: 11/660,131

(22) PCT Filed: Aug. 5, 2005

(86) PCT No.: PCT/JP2005/014389
§ 371 (c)(1),
(2), (4) Date: Nov. 5, 2007

(87) PCT Pub. No.: WO2006/016530
PCT Pub. Date: Feb. 16, 2006

(65) Prior Publication Data
US 2008/0260848 A1    Oct. 23, 2008

(30) Foreign Application Priority Data
Aug. 10, 2004   (JP) ................... 2004-233660

(51) Int. Cl.
*A61K 9/14*     (2006.01)
*A61K 38/00*    (2006.01)
*A61K 31/4035*  (2006.01)
*A61F 13/00*    (2006.01)
*A61K 9/50*     (2006.01)

(52) U.S. Cl.
USPC ............... 424/499; 424/434; 514/2; 514/417

(58) Field of Classification Search
USPC ................ 424/499, 434; 514/2, 417
See application file for complete search history.

(56) References Cited

U.S. PATENT DOCUMENTS

| | | |
|---|---|---|
| 3,906,950 A | 9/1975 | Cocozza |
| 4,013,075 A | 3/1977 | Cocozza |
| 4,159,345 A | 6/1979 | Takeo et al. |
| 4,226,233 A | 10/1980 | Kritzer |
| 4,300,545 A | 11/1981 | Goodnow et al. |
| 4,613,500 A | 9/1986 | Suzuki et al. ............ 429/85 |
| 4,889,114 A | 12/1989 | Kladders |
| 5,098,907 A | 3/1992 | Kondo et al. |

(Continued)

FOREIGN PATENT DOCUMENTS

| | | |
|---|---|---|
| EP | 0122036 A1 | 10/1984 |
| EP | 0147755 A2 | 7/1985 |

(Continued)

OTHER PUBLICATIONS

Rowe, et al (Eds). 'Handbook of Pharmaceutical Excipients. Pharmaceutical Press. 2003. p. 108-109.

(Continued)

*Primary Examiner* — Ernst Arnold
*Assistant Examiner* — Hong Yu
(74) *Attorney, Agent, or Firm* — Wilson, Sonsini, Goodrich & Rosati, P.C.

(57) ABSTRACT

Powdery compositions for intranasal administration, which comprise non-peptide/non-protein drugs and as a carrier, crystalline cellulose aggregates having a particular cribriform particle diameter, yield rapid action and high absorbability of the drugs.

8 Claims, 4 Drawing Sheets

(56) References Cited

U.S. PATENT DOCUMENTS

| | | | |
|---|---|---|---|
| 5,320,094 A | 6/1994 | Laube et al. | |
| 5,419,315 A | 5/1995 | Rubsamen | |
| 5,647,349 A | 7/1997 | Ohki et al. | |
| 5,672,581 A | 9/1997 | Rubsamen et al. | |
| 5,674,507 A | 10/1997 | Banker et al. | |
| 5,683,361 A | 11/1997 | Elk et al. | |
| 5,731,303 A | 3/1998 | Hsieh | |
| 5,756,483 A | 5/1998 | Merkus et al. | |
| 5,804,209 A | 9/1998 | De Ponti et al. | |
| 5,810,004 A | 9/1998 | Ohki et al. | |
| 5,939,100 A | 8/1999 | Albrechtsen et al. | |
| 5,942,242 A | 8/1999 | Mizushima et al. | |
| 5,948,749 A | 9/1999 | Igarashi et al. | |
| 5,958,458 A | 9/1999 | Norling et al. | |
| 5,989,217 A | 11/1999 | Ohki et al. | |
| 6,136,295 A | 10/2000 | Edwards et al. | |
| 6,197,328 B1 * | 3/2001 | Yanagawa | 424/434 |
| 6,248,363 B1 | 6/2001 | Patel et al. | |
| 6,273,086 B1 | 8/2001 | Ohki et al. | |
| 6,298,846 B1 | 10/2001 | Ohki et al. | |
| 6,516,795 B1 | 2/2003 | Bougamont et al. | |
| 6,815,424 B2 | 11/2004 | Vickery et al. | |
| 6,824,080 B2 | 11/2004 | Matsugi et al. | |
| 6,835,389 B1 | 12/2004 | Dohi et al. | 424/434 |
| 6,855,913 B2 | 2/2005 | Nikodym | |
| 6,906,027 B2 | 6/2005 | Oki et al. | |
| 7,278,982 B2 | 10/2007 | Tsutsui | |
| 7,306,787 B2 | 12/2007 | Tarara et al. | |
| 7,353,823 B2 | 4/2008 | Tsutsui | |
| 7,638,138 B2 | 12/2009 | Oki et al. | |
| 7,806,117 B2 | 10/2010 | Tsutsui | |
| 2001/0027301 A1 | 10/2001 | Lau et al. | |
| 2001/0038824 A1 | 11/2001 | Horii et al. | |
| 2002/0002172 A1 | 1/2002 | Bell-Huff et al. | |
| 2002/0012688 A1 * | 1/2002 | Dohi et al. | 424/434 |
| 2002/0040139 A1 | 4/2002 | Billotte et al. | |
| 2003/0199424 A1 * | 10/2003 | Smith et al. | 514/1 |
| 2004/0063615 A1 | 4/2004 | Oki et al. | |
| 2004/0076588 A1 | 4/2004 | Batycky et al. | |
| 2004/0092428 A1 * | 5/2004 | Chen et al. | 514/2 |
| 2004/0173211 A1 | 9/2004 | Kladders et al. | |
| 2005/0022812 A1 | 2/2005 | Hrkach | |
| 2005/0042177 A1 | 2/2005 | Ryde et al. | |
| 2005/0142073 A1 | 6/2005 | Watts et al. | |
| 2005/0177095 A1 | 8/2005 | Tsutsui | |
| 2006/0106057 A1 | 5/2006 | Daniel et al. | |
| 2006/0116657 A1 | 6/2006 | Schmid | |
| 2006/0216352 A1 | 9/2006 | Nystrom et al. | |
| 2006/0217658 A1 | 9/2006 | Tsutsui | |
| 2006/0233715 A1 | 10/2006 | Oki et al. | |
| 2007/0055200 A1 | 3/2007 | Gilbert | |
| 2007/0060868 A1 | 3/2007 | Tsutsui et al. | |
| 2007/0085509 A1 | 4/2007 | Schon et al. | |
| 2007/0184109 A1 | 8/2007 | Floyd et al. | |
| 2007/0249674 A1 | 10/2007 | Bolton et al. | |
| 2007/0272763 A1 | 11/2007 | Dunne et al. | |
| 2008/0031959 A1 | 2/2008 | Blondino et al. | |
| 2008/0090841 A1 | 4/2008 | Johnson et al. | |
| 2008/0127972 A1 | 6/2008 | Morton | |
| 2008/0286362 A1 | 11/2008 | Baran, Jr. et al. | |
| 2009/0157037 A1 | 6/2009 | Iyer et al. | |
| 2009/0169640 A1 | 7/2009 | Oki et al. | |
| 2010/0178331 A1 | 7/2010 | Nagata et al. | |
| 2011/0033544 A1 | 2/2011 | Nagata et al. | |
| 2011/0045088 A1 | 2/2011 | Tsutsui et al. | |

FOREIGN PATENT DOCUMENTS

| | | | |
|---|---|---|---|
| EP | 0761248 A1 | 3/1997 | |
| EP | 0943326 A1 | 9/1999 | |
| EP | 1025859 A1 | 8/2000 | |
| EP | 1 108 423 A1 | 6/2001 | |
| EP | 1454648 A1 | 9/2004 | |
| EP | 1504780 A1 | 2/2005 | |
| EP | 1785145 A1 | 5/2007 | |
| GB | 2395900 A | 6/2004 | |
| JP | 3912469 | 7/1964 | |
| JP | 53127553 | 11/1978 | |
| JP | 54062328 | 5/1979 | |
| JP | 59-34267 A | 2/1984 | |
| JP | 59-163313 A | 9/1984 | |
| JP | 60-185564 | 9/1985 | |
| JP | 60-224616 | 11/1985 | |
| JP | 62-42888 | 9/1987 | |
| JP | 63267731 | 11/1988 | |
| JP | 3-29146 | 3/1991 | |
| JP | 5-32560 | 2/1993 | |
| JP | 7-165613 A | 6/1995 | |
| JP | 8-098888 | 4/1996 | |
| JP | H 08-206208 A | 8/1996 | |
| JP | 08243164 | 9/1996 | |
| JP | 9-276405 | 10/1997 | |
| JP | 9291026 A | 11/1997 | |
| JP | 10059841 A | 3/1998 | |
| JP | 11/216357 | 8/1999 | |
| JP | 11-322582 | 11/1999 | |
| JP | 2000229859 A | 8/2000 | |
| JP | 2000-239187 | 9/2000 | |
| JP | 200155323 A | 2/2001 | |
| JP | 2002255795 A | 9/2002 | |
| JP | 2003-154006 A | 5/2003 | |
| JP | 2003-175103 A | 6/2003 | |
| JP | 2003206227 A | 7/2003 | |
| WO | WO 94/04133 A1 | 3/1994 | |
| WO | WO 95/12399 A1 | 5/1995 | |
| WO | WO 95/34582 A1 | 12/1995 | |
| WO | WO 97/31626 A1 | 9/1997 | |
| WO | WO 98/30207 A1 | 7/1998 | |
| WO | WO 99/16422 A1 | 4/1999 | |
| WO | WO 99/16470 A1 | 4/1999 | |
| WO | WO 00/12063 A1 | 3/2000 | |
| WO | WO 00/12136 A1 | 3/2000 | |
| WO | WO 00/23023 A1 | 4/2000 | |
| WO | WO 00/38811 A1 | 7/2000 | |
| WO | WO 01/26630 A1 | 4/2001 | |
| WO | WO 01/32125 A2 | 5/2001 | |
| WO | WO 02/094233 A1 | 11/2002 | |
| WO | WO 03/004048 A1 | 1/2003 | |
| WO | WO 2008/031028 A2 | 3/2003 | |
| WO | WO 03/095008 A1 | 11/2003 | |
| WO | WO 2004/004922 A1 | 1/2004 | |
| WO | WO 2004/073729 A1 | 9/2004 | |
| WO | WO 2005/056008 A1 | 6/2005 | |
| WO | WO 2005/104712 A2 | 11/2005 | |
| WO | WO 2006/016530 A1 | 2/2006 | |
| WO | WO 2006/040680 A1 | 4/2006 | |
| WO | WO 2008/075102 A1 | 6/2008 | |
| WO | WO 2008/078730 A1 | 7/2008 | |
| WO | WO 2008/031028 A3 | 11/2008 | |
| WO | WO 2009/095684 A1 | 8/2009 | |

OTHER PUBLICATIONS

European search report dated Jul. 15, 2008 for Application No. 05768543.0.

International search report dated Nov. 1, 2005 for PCT Application No. JP2005/014389.

Office action dated Sep. 28, 2011 for JP Application No. 2006-531575 (in Japanese with English translation).

UK search report dated Sep. 9, 2011 for Application No. GB1012959.1.

European search report and opinion dated Dec. 19, 2011 for Application No. 07860016.0.

"Fluorouracil" definition viewed on the National Cancer Institute website at www.cancergov/drugdictionary?cdrid=43130 on May 31, 2012.

European office action dated Jun. 25, 2012 for Application No. 05768543.0.

Hens, et al., "BMP4 and PTHrP interact to stimulate ductal outgrowth during embryonic mammary development and to inhibit hair follicle induction," Development 2007, 234, pp. 1221-1230.

(56) References Cited

OTHER PUBLICATIONS

Merriam-Webster's Collegiate Dictionary, 10th edition, Merriam-Webster Incorporated: Springfield, Massachusetts, 1993, pp. 41.
International search report (partial) dated Dec. 21, 2010 for PCT Application No. IB2010/02168.
UK combined office action and search report dated Nov. 10, 2010 for Application No. GB1012959.1.
U.S. Appl. No. 12/576,219, filed Oct. 8, 2009, Tsutsui et al.
International search report and written opinion dated Jun. 28, 2011 for PCT Application No. IB2010/02168.
U.S. Appl. No. 13/649,515, filed Oct. 11, 2012, Nagata et al.
U.S. Appl. No. 13/827,859, filed Mar. 14, 2013, Oki et al.
Advisory action dated Sep. 13, 2013 for U.S. Appl. No. 12/848,850.
Hibberd, et al. Immunization strategies for the immunocompromised host: the need for immunoadjuvants. Ann Intern Med. Jun. 15, 1989;110(12):955-6.
Ishikawa, et al. Improved nasal bioavailability of elcatonin by insoluble powder formulation. Int J Pharm. Aug. 14, 2001;224(1-2):105-14.
Office action dated Jan. 13, 2011 for U.S. Appl. No. 12/346,537.
Office action dated Jan. 20, 2011 for U.S. Appl. No. 12/576,219.
Office action dated Jan. 29, 2008 for U.S. Appl. No. 10/545,764.
Office action dated Mar. 4, 2013 for U.S. Appl. No. 12/848,850.
Office action dated Apr. 12, 2012 for U.S. Appl. No. 12/576,219.
Office action dated Apr. 20, 2012 for U.S. Appl. No. 12/780,433.
Office action dated Jun. 4, 2012 for U.S. Appl. No. 12/521,116.
Office action dated Jun. 10, 2013 for U.S. Appl. No. 12/576,219.
Office action dated Jun. 25, 2012 for U.S. Appl. No. 12/346,537.
Office action dated Sep. 6, 2011 for U.S. Appl. No. 12/346,537.
Office action dated Sep. 6, 2011 for U.S. Appl. No. 12/576,219.
Office action dated Sep. 20, 2013 for U.S. Appl. No. 13/827,859.
Office action dated Sep. 24, 2008 for U.S. Appl. No. 10/545,764.
Office action dated Oct. 10, 2012 for U.S. Appl. No. 12/780,433.
Office action dated Oct. 15, 2012 for U.S. Appl. No. 12/848,850.
Office action dated Dec. 5, 2011 for U.S. Appl. No. 12/346,537.
U.S. Appl. No. 10/512,857, filed May 13, 2003, in the name of Tatsuo Tsuisui.
International search report dated May 7, 2003 for PCT Application No. JP2003/001948.
International search report dated Feb. 5, 2008 for PCT Application No. JP2007/074787.
International search report Jun. 8, 2010 for PCT Application No. JP2010/003285.
Kleinebudde, et al. Influence of degree of polymerization on behavior of cellulose during homogenization and extrusion/spheronization. AAPS Pharmasci 2000, 2(2) Article 21, 1-10.
European search report and opinion mailed Dec. 20, 2013 for Application No. 10774745.3.

* cited by examiner

COMPOSITIONS THAT ENABLE RAPID-ACTING AND HIGHLY ABSORPTIVE INTRANASAL ADMINISTRATION

TECHNICAL FIELD

The present invention relates to powder form pharmaceutical compositions delivered via nasal mucosa. More specifically, the present invention relates to powdery compositions for intranasal administration which enable both rapid action and high absorbability of non-peptide/non-protein drugs.

BACKGROUND ART

The nasal route of drug administration has long been used where local action of drug is anticipated such as in rhinitis treatments. Recently, various studies were carried out on intranasal drug administration that is expected to have systemic effects because a) the nasal mucosa has a well developed vascular network and is thus histologically advantageous for drug absorption; b) drugs absorbed through the nasal mucosa can avoid first-pass metabolism in the gastrointestinal tract and liver; c) it is self-administrable and painless.

Interesting results obtained by those studies include a particularly preferred embodiment of a rapid-acting and prolonged-acting intranasal composition, which combines a base that is water-absorbing and water-insoluble and has 90% (w/w) or more of particles with a diameter in the range of 10 to 100 μm, and a base that is water-absorbing and gel-forming and has 90% (w/w) or more of particles with a diameter in the range of 50 to 350 μm (see Patent Document 1). It is clear from the Examples of Patent Document 1 that the formulation of 60 to 95% (w/w) hydroxypropyl cellulose (a water-absorbing and gel-forming base) and crystalline cellulose (a water-absorbing and water-insoluble base) does not change drug persistence, but shows immediate drug absorption as compared with crystalline cellulose base alone.

In another particularly preferred embodiment, an intranasal composition with improved drug absorbance is proposed. The composition is a combination of a water-absorbing and water-insoluble base that has 90% (w/w) or more of particles with a diameter in the range of 10 to 250 μm, and a water-absorbing and gel-forming base that has 90% (w/w) or more of particles with a diameter in the range of 10 to 50 μm. Patent Document 2 states that particles of 150 μm or more shall be actively used as a water-absorbing and water-insoluble base such as crystalline cellulose or the like. According to the Examples of Patent Document 2, when compared with crystalline cellulose base alone, a higher maximum drug level in blood is achieved if crystalline cellulose (a water-absorbing and water-insoluble base) is combined with 5 to 40% (w/w) hydroxypropyl cellulose (a water-absorbing and gel-forming base).

Furthermore, an intranasal insulin preparation proposed by the present applicants is also known. The preparation uses as a carrier, a crystalline cellulose aggregate in which 85% (w/w) or more of the particles have a cribriform particle diameter within the entire or partial range of 20 to 60 μm. The particles are substantially the same as those used in the present invention. The present applicants succeeded in improving insulin absorption with the preparation (see Patent Document 3).

[Patent Document 1] Japanese Patent Application Kokai Publication No. (JP-A) H9-291026 (unexamined, published Japanese patent application)

[Patent Document 2] JP-A H10-59841 (corresponding to EP-A1-943326)

[Patent Document 3] WO 03/004048A1 (corresponding to EP-A1-1413311)

DISCLOSURE OF THE INVENTION

Problems to be Solved by the Invention

As described above, it is known that intranasal compositions for particular drugs using a given carrier can achieve specific objectives. Nonetheless, the present inventors predicted that among such drugs, some that are particularly expected to have systemic effects can have enhanced drug efficacy and utility value when used as intranasal compositions.

First, the present inventors focused on opioid analgesic agents such as morphine. Morphine plays a central role in the pain treatment of cancer patients. Various types of morphine preparations, such as sustained-release oral preparations which continuously relieve pain, are commercially available. However, most of those preparations are long-acting preparations for alleviating constant or continuous pain. Besides injections, the only rapid-acting preparations for acute pain that suddenly strikes the patients are suppositories, oral solutions, and the like. Thus, there are strong demands for administration methods that are rapid-acting, effective, simple and convenient and which can be self-administered. Further, opioid analgesic agents such as morphine are problematic in that they have decreased bioavailability because they are significantly affected by the first-pass metabolism in liver and mucosal epithelia of the gastrointestinal tract after oral administration. Accordingly, the oral dosage is gradually increased and as a result, patients suffer from frequent occurrence of the adverse effects (in contrast to analgesic effects) of morphine such as constipation, nausea, vomiting, thirst, loss of appetite and the like. In view of the above circumstances, if successfully developed, a rapid-acting intranasal preparation that can avoid first-pass metabolism and be administered by a simple and convenient procedure, can be used as an administration method to improve patient's QOL and thus to contribute to the advancement of the technical field.

Meanwhile, the present inventors focused on antiemetic agents such as tropisetron, as a drug that is expected to have systemic effects. Tropisetron plays an important role in preventing nausea and vomiting which are adverse effects of cancer chemotherapy. Oral tropisetron preparations are used routinely. However, such oral preparations take a long time to exert their effect, and therefore it is difficult to immediately alleviate the troubling nausea and vomiting. Furthermore, since symptoms of nausea and vomiting impair patients' ability to swallow oral drugs, there are demands for non-oral, rapid-acting parenteral self-administrable administration methods.

For example, Patent Documents 1 and 2 shown above teach how to achieve rapid action. The present inventors examined if the methods described in these documents can provide intranasal compositions comprising morphine, tropisetron, or the like, but could not find satisfactory compositions. Through further investigations, the present inventors discovered that the use of a carrier, which is substantially the same as the crystalline cellulose specified in Patent Document 3 that enables high intranasal absorbability of insulin, a peptide/protein drug, enables high absorbability as well as rapid action of non-peptide/non-protein drug comparable to that of parenteral administration, thereby completed the present invention.

Thus, the present invention provides powdery compositions for intranasal administration which comprise a non-peptide/non-protein drug, and crystalline cellulose aggregate as a carrier thereof. 85% (w/w) or more of the crystalline cellulose aggregate are particles that have a cribriform particle diameter within the entire range of 20 to 60 μm or a partial range thereof.

In other words, the present invention provides powdery compositions for intranasal administration that comprise a non-peptide/non-protein drug and crystalline cellulose aggregate as a carrier, in which 85% (w/w) (ratio in terms of the total crystalline cellulose aggregate) or more of the crystalline cellulose aggregate have a cribriform particle diameter within the entire range of 20 to 60 μm or a partial range thereof.

Furthermore, in a preferred embodiment, the present invention provides the above-described compositions using a crystalline cellulose aggregate of which, 25% (w/w) or less are particles with a cribriform particle diameter of less than 25 μm;

20 to 60% (w/w) are particles with a cribriform particle diameter of 25 to 38 μm;

20 to 60% (w/w) are particles with a cribriform particle diameter of 38 to 53 μm; and the remainder are particles with a cribriform particle diameter of 53 μm or greater, wherein the ratio of the total crystalline cellulose aggregate is taken as 100% (w/w).

One or more of the non polypeptide/non-protein drug used for the intranasal compositions provided in the present invention can be selected from the following examples without being construed as limiting: antibiotics, antifungal agents, sulfa drugs, antituberculosis drugs, antimicrobial agents, antiviral agents, hypnotic sedatives, antiepileptic agents, narcotic analgesics, nonnarcotic analgesics, sedative drugs, psychotherapeutic agents, muscle relaxants, antiallergic agents, anti-rheumatic drugs, cardiotonic drugs, antiarrhythmic agents and antihypertensive agents, diuretic agents, coronary vasodilators, antidementia drugs, brain activators, brain circulation ameliorating agents, antiparkinsonian agents, antihyperlipidemic drugs, antiulcer drugs, antiemetic agents, obesity drugs, diabetic drugs, hemostatic drugs, antithrombotic agents, migraine drugs, antitussive drugs and expectorants, respiratory stimulants, asthma drugs, antidiarrheal drugs, nonsteroidal antiinflammatory agents, antipodagrics, therapeutic agents for urinary diseases, drugs for improving sexual function, agents for the uterus, steroids, prostaglandins, vitamins, histamines, antidotes, therapeutic agents for heavy metal toxification, quit smoking agents, antianaphylactic agents, and antitumor agents.

Specifically, such non-peptide/non-protein drugs include, for example, antibiotics such as penicillins, carbapenems, cephems, aminoglycosides, macrolides, tetracyclines, and chloramphenicols; antifungal agents such as amphotericin B, griseofulvin, nystatin, fluconazole, flucytosine, and miconazole; sulfa drugs such as salazosulfapyridine and sulfamethoxazole; antituberculosis drugs such as isoniazid, ethambutol, and rifampicin; antimicrobial agents such as enoxacin, ofloxacin, ciproflaxacin, tosufloxacin, and norfloxacin; antiviral agents such as vidarabine, aciclovir, didanosine, zidovudine, oseltamivir, zanamivir, and valganciclovir; sleep aids such as brotizolam, triazolam, and zopiclone; antiepileptic agents such as carbamazepine, clonazepam, zonisamide, valproic acid, phenytoin, phenobarbital, and primidone; narcotic analgesics such morphine, fentanyl, and pethidine; nonnarcotic analgesics such as buprenorphine, pentazocine, and tramadol hydrochloride; sedative drugs such as midazolam; psychotherapeutic agents such as chlorpromazine, haloperidol, tryptanol, imipramine, clomipramine, etizolam, oxazolam, and diazepam; muscle relaxants such as eperisone, tizanidine, baclofen, suxamethonium chloride, pancuronium bromide, and dantrolene; antiallergic agents such as chlorpheniramine, cyproheptadine, mequitazine, diphenhydramine, and sodium cromoglycate; anti-rheumatic drugs such as auranofin, bucillamine, and D-penicillamine; cardiotonic drugs such as digoxin and digitoxin; antiarrhythmic agents and antihypertensive agents such as atenolol, propranolol, metoprolol, amiodarone, quinidine, procainamide, mexiletine, nicardipine, enalapril, captopril, prazosin, hydralazine, reserpine, and clonidine; diuretic agents such as hydrochlorothiazide, potassium canrenoate, spironolactone, mannitol, acetazolamide, and furosemide; coronary vasodilators such as diltiazem, nifedipine, verapamil, and dipyridamole; antidementia drugs such as donepezil hydrochloride, galanthamine, and memantine; brain activators such as citicoline and tiapride; brain circulation ameliorating agents such as ATP, isosorbide, and nicergoline; antiparkinsonian agents such as trihexyphenidyl, biperiden, levodopa, dopamine, and amantadine; antihyperlipidemic drugs such as clofibrate and pravastatin; antitumor agents such as cimetidine, famotidine, omeprazole, lansoprazole, pirenzepine, aldioxa, sofalcone, and teprenone; antiemetic agents such as granisetron, ondansetron, tropisetron, cisapride, domperidone, and metoclopramide; obesity drugs such as mazindol; diabetic drugs such as pioglitazone hydrochloride, voglibose, gliclazide, acarbose, ciglitazone, sorbinil, glimepiride, epalrestat, ganglioside, midaglizole hydrochloride, and ponalrestat; hemostatic drugs such as cabazochrome and tranexamic acid; antithrombotic agents such as heparin, low-molecular-weight heparin, warfarin, cilostazol, ticlopidine, ethyl icosapentate, andberaprost; migraine drugs such as ergotamine, dihydroergotamine, and sumatriptan; antitussive drugs and expectorants such as codeine, tipepidine, dextromethorphan, acetylcysteine, carbocysteine, and bromhexine; respiratory stimulants, such dimorpholamine, doxapram, and naloxone; asthma drugs such as salbutamol, terbutaline, procaterol, theophylline, ephedrine, ibudilast, ketotifen, terfenadine, tranilast, and beclomethasone; antidiarrheal drugs such as loperamide; nonsteroidal antiinflammatory agents such as mefenamic acid, indomethacin, ibuprofen, ketoprofen, loxoprofen, and diclofenac; antipodagrics such as allopurinol, colchicine, and benzbromarone; therapeutic agents for urinary diseases such as estramustine, chlormadinone, flavoxate, and oxybutynin; drugs for improvement in sexual function such as sildenafil, vardenafil, and apomorphine; uterus acting drugs such asisoxsuprine, dinoprost, ritodrine, oestriol, and econazole; steroids such as dexamethasone, triamcinolone, hydrocortisone, prednisolone, testosterone, estradiol, and chlormadinone; prostaglandins such as alprostadil, limaprost, and dinoprost; vitamins such as retinol, thiamine, riboflavin, pyridoxal, cobalamine, and pantothenic acid; antidotes such as pralidoxime iodide methyl, protamine, and leucovorin; therapeutic agents for heavy metal toxification such as dimercaprol and sodium thiosulfate; quit smoking aid such as nicotine; antianaphylactic agents such as epinephrine; antitumor agents such as cyclophosphamide, dacarbazine, cytarabine, tegafur, 5-FU, methotrexate, mercaptopurine, epirubicin, doxorubicin, mitomycin, and etoposide.

Furthermore, non-peptide/non-protein drugs that require rapid-acting ability in therapy include the following: didanosine, zidovudine, lamivudine, atazanavir, nelfenavir, sanilvudine, emtricitabine, oseltamivir, zanamivir, valganciclovir, amantadine, ketamine, pentobarbital sodium, lidocaine, estazolam, midazolam, triazolam, nitrazepam, flunitrazepam, rilmazafone, zopiclone, brotizolam, chloral hydrate, carbamazepine, clonazepam, zonisamide, sodium valproate, phenytoin, phenobarbital, primidone, gabapentin, opium, morphine, ethylmorphine, oxycodone, codeine, dihydrocodeine, fentanyl, droperidol, levorphanol, methadone, meperidine, pethidine, buprenorphine, butorphanol, tramadol, nalfurafine, pentazocine, sulpyrine, aspirin, acetaminophen, ergotamine, dihydroergotamine, sumatriptan, eletriptan, zolmitriptan, rizatriptan, naratriptan, donepezil, suxamethonium, pancuronium, sildenafil, vardenafil, apomorphine, tadalafil, atropine, scopolamine, digitoxin, digoxin, methyldigoxin, isosorbide, nitroglycerin, quinidine, disopyramide, dopamine, dobutamine, epinephrine, etilefrine, norepinephrine, phenylephrine, dimorpholamine, doxapram, naloxone, flumazenil, tipepidine, dextromethorphan, ambroxol, bromhexine, salbutamol, terbutaline, procaterol, theophylline, ephedrine, sodium cromoglycate, ketotifen, oxatomide, tranilast, granisetron, azasetron, ramosetron, tropisetron, indisetron, palonosetron, cisapride, domperidone, metoclopramide, trimebutine, loperamide, mefenamic acid, indomethacin, sulindac, ibuprofen, ketoprofen, naproxen, pranoprofen, loxoprofen, diclofenac, tiaprofenic acid, tiaramide, carbazochrome sulfonic acid, tranexamic acid, pralidoxime iodide methyl, protamine, leucovorin, dimercaprol, deferoxamine, and sodium thiosulfate.

Furthermore, such non-peptide/non-protein drugs include, for example, the existing drugs that are administered by non-injection means, such as oral drugs and nasal drops, but cannot obtain satisfactory absorbability or rapid-acting ability.

Herein, the term "crystalline cellulose aggregate" generally includes purified water-insoluble fractions of partial acid-depolymerized α-cellulose, where the α-cellulose is obtained as pulp from fibrous plants. The crystalline cellulose aggregate obtained from rayon fibers or the like can also be used as long as it serves the purpose of the present invention. More specifically, Avicel™ and the like, and derivatives thereof, as described in, for example, Japanese Patent Application Kokoku Publication No. (JP-B) S39-12469 (examined, approved Japanese patent application published for opposition), JP-B S56-38128, JP-B S61-21201, and JP-B H5-38732, can be used as needed to obtain crystalline cellulose aggregates for use in the present invention, by reducing the particle size with a high-speed rotating impact mill or air mill to increase the bulk density, finely grinding the particles, and then sifting or sorting the particles into aggregates of particles with desirable size.

Such crystalline cellulose aggregates can usually be obtained by depolymerization as described above; however, the average polymerization degree is not particularly limited as long as it serves the purpose of the present invention. Generally, crystalline cellulose aggregates that have an average polymerization degree of 15 to 400, preferably of 80 to 350, more preferably of 100 to 300 can be selected in the present invention. Such crystalline cellulose aggregates include those whose bulk density is 0.13 to 0.65 g/cm$^3$ and preferably 0.18 to 0.35 g/cm$^3$, without being limited thereto. The bulk densities shown above are values determined by using Scott Volumeter for measurement.

Factors that are important for determining whether a crystalline cellulose aggregate can be used in the present invention are size and distribution patterns of the crystalline cellulose particles constituting the aggregate. In terms of the cribriform particle diameter, 85% (w/w) (ratio in terms of the total crystalline cellulose aggregate) or more of the particles are required to be in the entire range of 20 to 60 μm, or a partial range thereof. Crystalline cellulose aggregates used in the present invention have a particular range of cribriform particle diameters. In the present invention, the powdery compositions for intranasal administration exert high absorbability and excellent rapid-acting ability for non-peptide/non-protein drugs.

Hereinafter, particle diameter refers to "cribriform particle diameter" unless otherwise stated.

Such aggregates can be used in combination with non-peptide/non-protein drugs. The phrase "within the entire range or a partial range thereof" is intended to mean, for example, a particle distribution where 90% (w/w) of particles or more have a particle size within the entire range of 10 to 100 μm, or a partial range thereof, for example, 20 to 60 μm. According to the present invention, the above-described particle diameter range is preferably the entire range of 20 to 60 μm or a partial range thereof.

Specifically, such crystalline cellulose aggregates include, for example, crystalline cellulose products which are available as Avicel™ PH-105 and PH-F20 at FMC corp. (US) and Asahi Kasei, respectively, in an intact form or in a sorted form. Although the preferred embodiments of the compositions in JP-A H10-59841 (or EP-A-943326) above use crystalline cellulose aggregates having such a particle diameter range in combination with a water-absorbing and gel-forming base, the document also describes the use of crystalline cellulose having a particle diameter range of 10 to 250 μm, as well as the use of crystalline cellulose having a particle diameter of 100 to 250 μm or 50 to 350 μm for low-molecular-weight drugs in the Examples. Thus, the compositions of the present invention can be said to be unique in using crystalline cellulose aggregates having the above-described diameter ranges independently.

More specifically, particularly preferred crystalline cellulose aggregates that can be used to exert such effects include, but are not limited to, crystalline cellulose aggregates of which 25% (w/w) or less are particles with a cribriform particle diameter of less than 25 μm;
20 to 60% (w/w) are particles with a cribriform particle diameter of 25 to 38 μm;
20 to 60% (w/w) are particles with a cribriform particle diameter of 38 to 53 μm; and
the remainder are particles with a cribriform particle diameter of 53 μm or greater,
wherein the ratio of the total crystalline cellulose aggregate is taken as 100% (w/w).

With such cribriform particle diameter range, the powdery compositions for intranasal administration in the present invention can exert high absorbability and excellent rapid-acting ability for non-peptide/non-protein drugs.

The compositions of the present invention can be prepared using a conventional means for homogeneously combining powdery drugs with a solid carrier (for example, an automatic mortar, mixing device, or mixer). Steps for removing particles with a diameter less than 10 μm may be added; however, from the inventors' experiences, such removal steps were unnecessary in most cases.

In other methods or embodiments, the compositions of the present invention may comprise other carriers or bases, pH adjustors, excipients, preservatives, stabilizers, lubricants, absorbefacients and such in addition to the ingredients described above, as long as they do not adversely affect the purpose of the present invention. Such carriers and bases include, for example, hydroxypropyl cellulose, alginic acid, polyvinylpyrrolidone, chitosan, gamma-polyglutamic acid, and arabic gum. Such preservatives include benzalkonium chloride and the like. Such lubricants include magnesium stearate and the like. Such absorbefacients include Angelica essential oil (main ingredient: cyclopentadecanolide) as described in U.S. Pat. No. 5,731,303.

In the present invention, the powdery compositions for intranasal administration also enable effective treatment of patients with a disease that particularly requires rapid-acting ability and high absorbability of drugs through intranasal administration.

Any devices may be used to perform an intranasal administration, as long as the device can efficiently deliver the powder intranasal compositions of the present invention to the nasal mucosa through intranasal administration. For example, Jetlizer (Unisia Jecs Co.) can be used.

The optimal dosage or required dosage for disease treatment cannot be specified, as it varies depending on the type of disease, patient's condition, severity of the disease, administration schedule and the like. Experts can readily determine the dosage as necessary, by referring to the results described in the Examples herein, and considering the blood concentration, efficacy of the drug, and other factors after a standard subcutaneous injection.

The type of diseases which particularly require rapid-acting ability and high absorbability of drugs for treatment is not particularly limited, and may be any diseases to which the above-described non-peptide/non-protein drugs are applicable. Such diseases include all diseases where patients are under a condition that requires particularly rapid-acting ability and high absorbability in treatment.

Thus, the present invention also relates to methods for treating diseases that require rapid-acting ability and high absorbability in therapy, by administering effective doses of the above-described powdery compositions for intranasal administration into patients' nasal cavity. Furthermore, the present invention relates to the use of the above-described powdery compositions for intranasal administration in producing pharmaceuticals for diseases that particularly require rapid-acting ability and high absorbability in treatment.

All the prior art documents cited herein are incorporated by reference.

Effects of the Invention

The present invention provides rapid-acting, highly absorptive powdery compositions for intranasal administration that enable rapid increase of drug concentration in blood immediately after administration.

BEST MODE FOR CARRYING OUT THE INVENTION

Herein below, the present invention will be described in more detail with reference to specific test examples of compositions for the intranasal delivery of various drugs in the present invention, but is not construed as being limited thereto. A single dose of an intranasal delivery composition was nasally administered to cynomolgus monkeys (body weight: 4.3 to 7.2 kg). Each composition was encapsulated and administered nasally using a device for nasal administration (Bioactis Co. Ltd.).

(1) Experiment of the Intranasal Administration of Morphine in Cynomolgus Monkeys

EXAMPLE 1

65 mg of morphine hydrochloride (equivalent to 50 mg of morphine free base) (Takeda Pharmaceutical Company), which is a narcotic analgesic, and 135 mg of crystalline cellulose (Asahi Kasei: Avicel™ PH-F20) were mixed thoroughly in a mortar. The obtained morphine composition was prepared and 5.2 mg morphine hydrochloride (equivalent to 4.0 mg of morphine free base) per head was administered nasally to male cynomolgus monkeys weighing from 5.5 to 6.2 kg (n=3).

The above-described crystalline cellulose used in the Examples herein is a crystalline cellulose aggregate, in which 90% (w/w) or more are particles that have a cribriform particle diameter within the range of 20 to 60 µm, more specifically, in which 6.8% (w/w) are particles with a cribriform particle diameter of less than 25 µm;

49.7% (w/w) are particles with a cribriform particle diameter of 25 to 38 µm;

36.9% (w/w) are particles with a cribriform particle diameter of 38 to 53 atm; and 6.6% (w/w) are particles with a cribriform particle diameter of 53-µm or greater.

Meanwhile, the bulk density of the crystalline cellulose aggregate was 0.21 g/cm$^3$, and the average polymerization degree of the aggregate was 100 to 300. Herein below, the parameters for crystalline cellulose used in the Examples are the same as the above.

CONTROL EXAMPLE 1

Morphine hydrochloride (Takeda Pharmaceutical Company) was dissolved in purified water to prepare a morphine injection solution (morphine concentration: 4 mg/ml). The preparation was administered subcutaneously to male cynomolgus monkeys weighing 5.4 and 6.1 kg (n=2), at 0.52 mg morphine hydrochloride (equivalent to 0.4 mg of morphine free base) per kg body weight.

The plasma concentration of morphine free base after administration was determined by the HPLC method.

Figure 1:
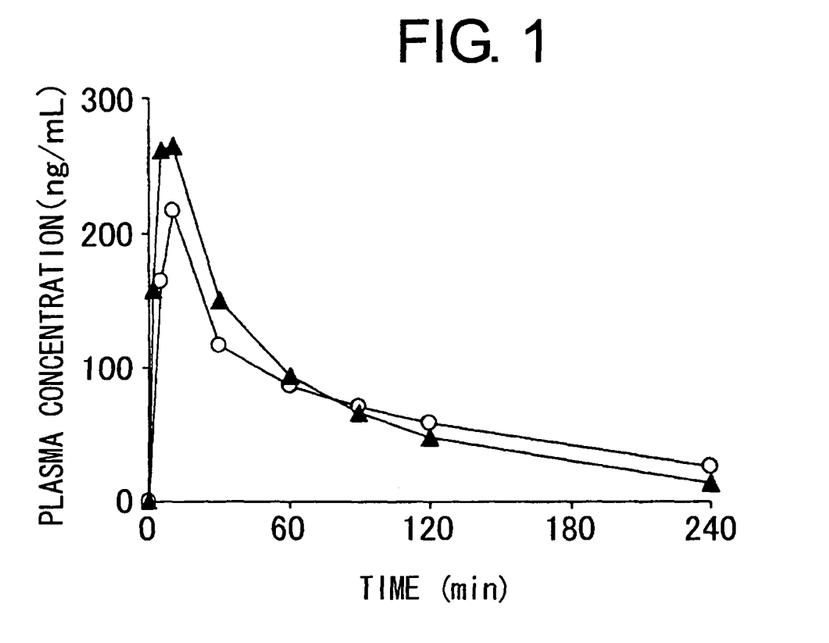
FIG. 1 shows a time course of the plasma concentration of morphine in cynomolgus monkeys. Open circle and closed triangle correspond to the results described in Example 1 and Control example 1 (average), respectively.

The time course of plasma morphine concentration for the above-described composition is shown in FIG. 1 and the corresponding raw data are shown in Tables 1 and 2. Pharmacokinetic parameters calculated based on the data are shown in Table 3.

TABLE 1

Example 1: Morphine composition
Plasma morphine concentration (ng/mL)

| Time (min) | Animal No. | | | |
|---|---|---|---|---|
| | No. 1 | No. 2 | No. 3 | Average |
| 5 | 172.4 | 181.6 | 141.8 | 165.2 |
| 10 | 295.6 | 205.3 | 150.8 | 217.2 |
| 30 | 123.3 | 117.6 | 111.6 | 117.5 |
| 60 | 94.4 | 80.7 | 85.4 | 86.8 |
| 90 | 80.5 | 65.1 | 68.8 | 71.5 |
| 120 | 59.4 | 58.6 | 55.4 | 57.8 |
| 240 | 29.4 | 21.5 | 26.1 | 25.7 |
| 480 | 6.8 | 6.5 | 8.1 | 7.1 |

TABLE 2

Control example 1: Morphine injection
Plasma morphine concentration (ng/mL)

| Time (min) | Animal No. | | |
|---|---|---|---|
| | No. 1 | No. 2 | Average |
| 2 | 175.3 | 141.0 | 158.1 |
| 5 | 277.5 | 245.0 | 261.3 |
| 10 | 232.8 | 295.2 | 264.0 |
| 30 | 151.4 | 149.6 | 150.5 |
| 60 | 104.5 | 82.4 | 93.5 |
| 90 | 68.8 | 63.7 | 66.3 |
| 120 | 46.2 | 48.8 | 47.5 |
| 240 | 15.1 | 13.3 | 14.2 |
| 480 | 6.2 | 4.3 | 5.2 |

TABLE 3

Pharmacokinetic parameters of morphine

| Composition | Dose | n | Cmax (ng/mL) | Tmax (min) | $AUC_{0-480}$ (ng·min/mL) | BA (%) |
|---|---|---|---|---|---|---|
| Example 1 | 4 mg/body (0.66 mg/kg) | 3 | 217.2 | 10.0 | 21038.5 | 63.6 |
| Control example 1 | 0.4 mg/kg | 2 | 286.4 | 7.5 | 20040.7 | — |

Note)
Cmax: Maximal plasma concentration
Tmax: Time required to reach the maximal plasma concentration
AUC: Area under plasma concentration vs. time curve
BA: Bioavailability The results in FIG. 1 and Tables 1 to 3 show that over the time course of average plasma concentrations of morphine, the post-intranasal administration plasma concentration of morphine reached 76% of the maximum plasma concentration 5 minutes after administration, and the maximum plasma concentration was achieved 10 minutes after administration. This post-intranasal administration plasma concentration pattern closely resembled the post-subcutaneous administration pattern. This shows that the intranasal administration of morphine was effective for acute pain in cancer patients immediately upon administration. Furthermore, the bioavailability of the intranasal composition was as high as 63.6% when compared with that of the subcutaneous administration. It was thus confirmed that the intranasal composition demonstrates high absorbability as well as rapid-acting ability.

(2) Experiment of the Intranasal Administration of Tropisetron in Cynomolgus Monkeys

EXAMPLE 2

27.5 mg of tropisetron hydrochloride (equivalent to 25 mg of tropisetron free base) (Sigma), which is an antiemetic agent, and 72.5 mg of crystalline cellulose (Asahi Kasei: Avicel™ PH-F20) were mixed thoroughly in a mortar. The obtained tropisetron composition was prepared and 4.4 mg tropisetron hydrochloride (equivalent to 4.0 mg of tropisetron free base) per head was administered nasally to male cynomolgus monkeys weighing from 6.3 to 7.2 kg (n=3).

CONTROL EXAMPLE 2

The same tropisetron hydrochloride as described in Example 2 was dissolved in purified water to prepare a tropisetron injection solution (tropisetron concentration: 2 mg/ml). The injection was given intravenously to male cynomolgus monkeys weighing 6.9 and 7.2 kg (n=2), at 0.22 mg tropisetron hydrochloride (equivalent to 0.20 mg of tropisetron free base) per kg weight.

The plasma concentration of tropisetron free base after administration was determined by the HPLC method.

Figure 2:
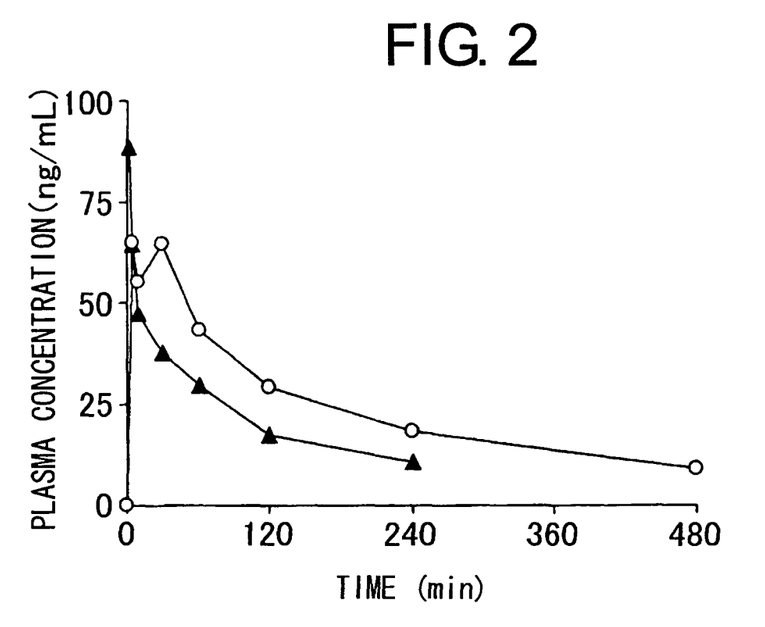
FIG. 2 shows a time course of the plasma concentration of tropisetron in cynomolgus monkeys. Open circle and closed triangle correspond to the results described in Example 2 and Control example 2 (average), respectively.

The time course of plasma tropisetron concentration for the above-described composition is shown in FIG. 2 and the corresponding raw data are shown in Tables 4 and 5. Pharmacokinetic parameters calculated based on the data are shown in Table 6. The time course of plasma tropisetron concentration after intravenous injection was subjected to a 2-compartment model analysis using the linear least-square method. The area under the theoretical plasma concentration vs. time curve (AUC) was determined based on the theoretical plasma tropisetron concentration calculated.

TABLE 4

Example 2: Tropisetron composition
Plasma tropisetron concentration (ng/mL)

| Time (min) | Animal No. | | | |
|---|---|---|---|---|
| | No. 1 | No. 2 | No. 3 | Average |
| 5 | 43.1 | 104.8 | 47.1 | 65.0 |
| 10 | 42.2 | 84.6 | 38.0 | 54.9 |
| 30 | 48.5 | 86.6 | 58.9 | 64.7 |
| 60 | 32.3 | 50.8 | 46.0 | 43.1 |
| 120 | 22.3 | 33.0 | 31.1 | 28.8 |
| 240 | 13.3 | 21.7 | 20.1 | 18.4 |
| 480 | 5.7 | 9.4 | 11.5 | 8.9 |

TABLE 5

Control example 2: Tropisetron injection
Plasma tropisetron concentration (ng/mL)

| Time (min) | Animal No. No. 1 | No. 2 | Average |
|---|---|---|---|
| 2 | 95.7 | 81.0 | 88.4 |
| 5 | 49.5 | 79.8 | 64.6 |
| 10 | 35.2 | 59.4 | 47.3 |
| 30 | 35.0 | 39.7 | 37.3 |
| 60 | 26.5 | 32.0 | 29.2 |
| 120 | 14.1 | 20.8 | 17.4 |
| 240 | 9.6 | 12.3 | 10.9 |

TABLE 6

Pharmacokinetic parameters of tropisetron

| Composition | Dose | n | Cmax (ng/mL) | Tmax (min) | $AUC_{0-480}$ (ng·min/mL) | BA (%) |
|---|---|---|---|---|---|---|
| Example 2 | 4 mg/body (0.59 mg/kg) | 3 | 70.7 | 21.7 | 15704.6 | 73.4 |
| Control example 2 | 0.2 mg/kg | 2 | — | — | 7392.0 | — |

Note)
Cmax: Maximal plasma concentration
Tmax: Time required to reach the maximal plasma concentration
AUC: Area under plasma concentration vs. time curve
BA: Bioavailability The results in FIG. 2 and Tables 4 to 6 show that over the time course of average plasma concentrations of tropisetron, the maximum plasma concentration was already achieved 5 minutes after intranasal administration. This post-intranasal administration plasma concentration pattern, which suggests immediate absorption, demonstrates that tropisetron became immediately effective for nausea and vomiting caused by chemotherapy in cancer patients. Furthermore, the bioavailability of the intranasal composition was as high as 73.4% when compared with that of the intravenous injection. It was thus confirmed that the intranasal composition demonstrates high absorbability as well as rapid-acting ability.

(3) Experiment of the Intranasal Administration of Oxycodone in Cynomolgus Monkeys

EXAMPLE 3

100 mg of oxycodone hydrochloride (equivalent to 90 mg of oxycodone free base) (Mallinckrodt Inc.), which is a narcotic analgesic, and 200 mg of crystalline cellulose (Asahi Kasei: Avicel™ PH-F20) were mixed thoroughly in a mortar. The obtained oxycodone composition was prepared and 16.7 mg oxycodone hydrochloride (equivalent to 15.0 mg of oxycodone free base) per head was administered nasally to male cynomolgus monkeys weighing from 4.9 to 5.2 kg (n=3).

COMPARATIVE EXAMPLE 3

Oxycodone hydrochloride (Mallinckrodt Inc.) was dissolved in purified water to prepare an oxycodone injection solution (oxycodone concentration: 25.0 mg/ml). The injection was given subcutaneously to male cynomolgus monkeys weighing 4.8 and 4.9 kg (n=2), at 2.8 mg oxycodone hydrochloride (equivalent to 2.5 mg of oxycodone free base) per kg weight.

The plasma concentration of oxycodone free base after administration was determined by the HPLC method.

Figure 3:
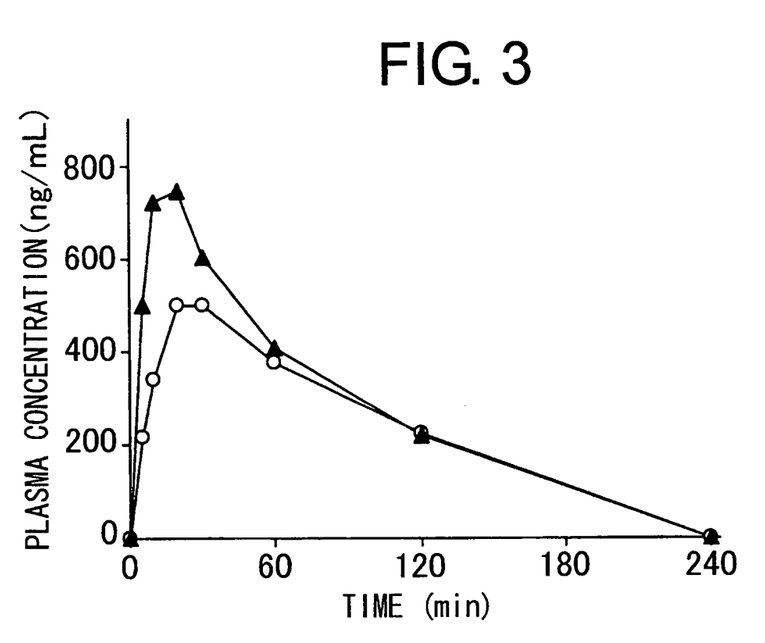
FIG. 3 shows a time course of the plasma concentration of oxycodone in cynomolgus monkeys. Open circle and closed triangle correspond to the results described in Example 3 and Control example 3 (average), respectively.

The time course of plasma oxycodone concentration for the above-described composition is shown in FIG. 3 and the corresponding raw data are shown in Tables 7 and 8. Pharmacokinetic parameters calculated based on the data are shown in Table 9.

TABLE 7

Example 3: Oxycodone composition
Plasma oxycodone concentration (ng/mL)

| Time (min) | Animal No. No. 1 | No. 2 | No. 3 | Average |
|---|---|---|---|---|
| 5 | 215.3 | 197.3 | 241.4 | 218.0 |
| 10 | 283.0 | 294.5 | 447.1 | 341.5 |
| 20 | 493.9 | 415.9 | 585.4 | 498.4 |
| 30 | 480.7 | 440.2 | 573.9 | 498.3 |
| 60 | 402.3 | 335.0 | 391.7 | 376.3 |
| 120 | 251.2 | 205.0 | 217.5 | 224.6 |
| 240 | —* | —* | —* | —* |

*Below detection limits

TABLE 8

Control example 3: Oxycodone injection
Plasma oxycodone concentration (ng/mL)

| Time (min) | Animal No. No. 1 | No. 2 | Average |
|---|---|---|---|
| 5 | 480.2 | 517.9 | 499.0 |
| 10 | 705.5 | 743.2 | 724.3 |
| 20 | 730.3 | 768.5 | 749.4 |
| 30 | 598.5 | 612.3 | 605.4 |
| 60 | 410.2 | 402.1 | 406.2 |
| 120 | 206.1 | 229.9 | 218.0 |
| 240 | —* | —* | —* |

*Below detection limits

TABLE 9

| | Pharmacokinetic parameters of oxycodone | | | | | |
|---|---|---|---|---|---|---|
| Composition | Dose | n | Cmax (ng/mL) | Tmax (min) | $AUC_{0-480}$ (ng · min/mL) | BA (%) |
| Example 3 | 15 mg/body (2.96 mg/kg) | 3 | 506.5 | 23.3 | 929.1 | 71.7 |
| Control example 3 | 2.5 mg/kg | 2 | 749.4 | 20.0 | 1088.8 | — |

Note)
Cmax: Maximal plasma concentration
Tmax: Time required to reach the maximal plasma concentration
AUC: Area under plasma concentration vs. time curve
BA: Bioavailability The results in FIG. 3 and Tables 7 to 9 show that over the time course of plasma concentrations of oxycodone, the post-intranasal administration concentration immediately increased and reached the maximum plasma concentration 20 minutes after administration. The post-intranasal administration plasma concentration pattern shows that the time required for achieving the maximal concentration is comparable to that for the subcutaneous administration. It demonstrates that immediately after intranasal administration, oxycodone became effective to acute pain in cancer patients. Furthermore, the bioavailability of the intranasal composition was as high as 71.7% when compared with that of the subcutaneous administration. It was thus confirmed that the intranasal composition demonstrates high absorbability as well as rapid-acting ability.

(4) Experiment of the Intranasal Administration of Fentanyl in Cynomolgus Monkeys

EXAMPLE 4

2.8 mg of fentanyl citrate (equivalent to 1.8 mg of fentanyl free base) (Fine Chemical Corp.), which is a narcotic analgesic, and 297.2 mg of crystalline cellulose (Asahi Kasei: Avicel™ PH-F20) were mixed thoroughly in a mortar. The obtained fentanyl composition was prepared and 0.47 mg fentanyl citrate (equivalent to 0.30 mg of fentanyl free base) per head was administered nasally to male cynomolgus monkeys weighing from 4.3 to 6.1 kg (n=3).

CONTROL EXAMPLE 4

The same fentanyl citrate as described in Example 4 was dissolved in purified water to prepare a fentanyl injection solution (fentanyl concentration: 0.5 mg/ml). The injection was given subcutaneously to male cynomolgus monkeys weighing 4.7 and 5.4 kg (n=2) at 0.079 mg fentanyl citrate (equivalent to 0.05 mg of fentanyl free base) per kg weight.

The plasma concentration of fentanyl free base after administration were determined by the HPLC method.

Figure 4:
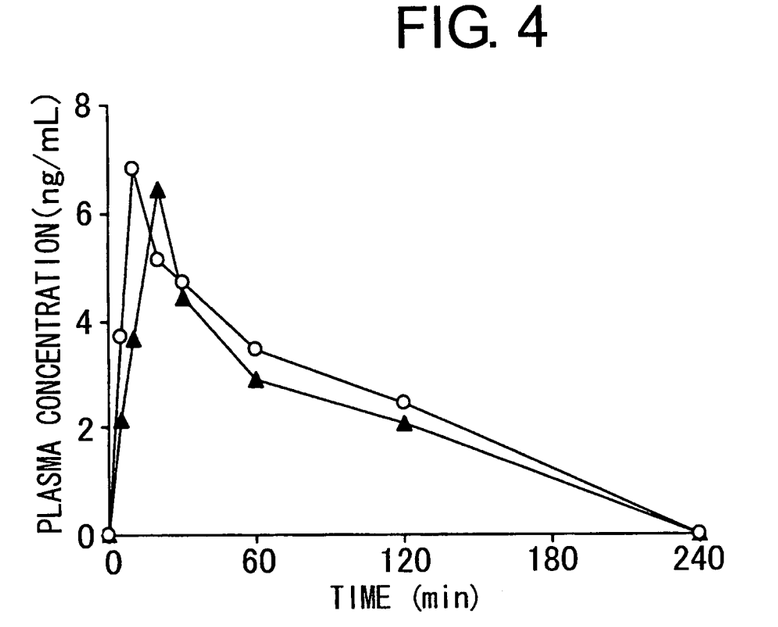
FIG. 4 shows a time course of the plasma concentration of fentanyl in cynomolgus monkeys. Open circle and closed triangle correspond to the results described in Example 4 and Control example 4 (average), respectively.

The time course of plasma fentanyl concentration for the above-described composition is shown in FIG. 4 and the corresponding raw data are shown in Tables 10 and 11. Pharmacokinetic parameters calculated based on the data are shown in Table 12.

TABLE 10

| | Example 4: Fentanyl composition Plasma fentanyl concentration (ng/mL) | | | |
|---|---|---|---|---|
| Time | Animal No. | | | |
| (min) | No. 1 | No. 2 | No. 3 | Average |
| 5 | 4.2 | 4.8 | 2.1 | 3.7 |
| 10 | 6.3 | 6.6 | 7.5 | 6.8 |
| 20 | 4.5 | 5.9 | 5.0 | 5.1 |
| 30 | 4.1 | 5.3 | 4.8 | 4.7 |
| 60 | 3.2 | 3.6 | 3.6 | 3.5 |
| 120 | 2.4 | 2.3 | 2.7 | 2.5 |
| 240 | —* | —* | —* | —* |

*Below detection limits

TABLE 11

| | Control example 4: Fentanyl injection Plasma fentanyl concentration (ng/mL) | | |
|---|---|---|---|
| Time | Animal No. | | |
| (min) | No. 1 | No. 2 | Average |
| 5 | 2.0 | 2.3 | 2.1 |
| 10 | 3.8 | 3.6 | 3.7 |
| 20 | 6.2 | 6.7 | 6.5 |
| 30 | 4.3 | 4.6 | 4.4 |
| 60 | 2.8 | 3.0 | 2.9 |
| 120 | 2.0 | 2.1 | 2.1 |
| 240 | —* | —* | —* |

*Below detection limits

TABLE 12

| | Pharmacokinetic parameters of fentanyl | | | | | |
|---|---|---|---|---|---|---|
| Composition | Dose | n | Cmax (ng/mL) | Tmax (min) | $AUC_{0-480}$ (ng · min/mL) | BA (%) |
| Example 4 | 0.30 mg/body (0.06 mg/kg) | 3 | 6.8 | 10 | 9.9 | 98.9 |

TABLE 12-continued

Pharmacokinetic parameters of fentanyl

| Composition | Dose | | n | Cmax (ng/mL) | Tmax (min) | $AUC_{0-480}$ (ng·min/mL) | BA (%) |
|---|---|---|---|---|---|---|---|
| Control example 4 | 0.05 | mg/kg | 2 | 6.5 | 20 | 8.5 | — |

Note)
Cmax: Maximal plasma concentration
Tmax: Time required to reach the maximal plasma concentration
AUC: Area under plasma concentration vs. time curve
BA: Bioavailability The results in FIG. 4 and Tables 10 to 12 show that over the time course of average plasma concentrations of fentanyl, the maximum plasma concentration was already reached 10 minutes after administration. This post-intranasal administration plasma concentration pattern shows that the time required to reach the maximal plasma concentration was shorter than that for the subcutaneous administration. It was thus demonstrated that when administered nasally, fentanyl became immediately effective for acute pain in cancer patients. Furthermore, the bioavailability of the intranasal composition was as high as 98.9% as compared with the subcutaneous administration. It was thus confirmed that the intranasal composition demonstrates high absorbability as well as rapid-acting ability.

INDUSTRIAL APPLICABILITY

As described above, the intranasal compositions of the present invention exhibit high absorbability as well as rapid-acting ability, and thus can be used to provide preparations of particular drugs to be administered in a new way of administration.

The invention claimed is:

1. A powdery composition for intranasal administration comprising:
   i) a non-peptide/non-protein drug, wherein the drug is an opioid receptor agonist, or a 5-hydroxytryptaminel (5-$HT_1$) receptor agonist; and
   ii) a carrier consisting essentially of crystalline cellulose aggregate, wherein 85% (w/w) or more of the crystalline cellulose aggregate has a particle size distribution of 20 to 60 μm and wherein when administered to a primate intranasally, the time to maximal blood concentration (Tmax) in said primate is achieved within 20 minutes.

2. The composition of claim 1, wherein Tmax is achieved within 10 minutes.

3. A powdery composition for intranasal administration comprising:
   i) a non-peptide/non-protein drug, wherein the drug is an opioid receptor agonist, or a 5-hydroxytryptaminel (5-$HT_1$) receptor agonist; and
   ii) a carrier consisting essentially of crystalline cellulose aggregate, wherein 85% (w/w) or more of the crystalline cellulose aggregate has a particle size distribution of 20 to 60 μm and wherein when administered to a primate intranasally, the absolute bioavailability (BA) of the drug is between 64% to 99%.

4. The powdery composition of claim 1 or 3, wherein the non-peptide/non-protein drug is sumatriptan, zolmitriptan, morphine or oxycodone.

5. The powdery composition of claim 1 or claim 3, wherein the non-peptide/non-protein drug is morphine.

6. The powdery composition of claim 1 or claim 3, wherein the non-peptide/non-protein drug is oxycodone.

7. The powdery composition of claim 1 or claim 3, wherein the non-peptide/non-protein drug is sumatriptan.

8. The powdery composition of claim 1 or claim 3, wherein the non-peptide/non-protein drug is zolmitriptan.

* * * * *

UNITED STATES PATENT AND TRADEMARK OFFICE
CERTIFICATE OF CORRECTION

PATENT NO.        : 8,673,360 B2                                                  Page 1 of 1
APPLICATION NO.   : 11/660131
DATED             : March 18, 2014
INVENTOR(S)       : Ryoichi Nagata et al.

It is certified that error appears in the above-identified patent and that said Letters Patent is hereby corrected as shown below:

In the Claims

COLUMN 15, LINE 41:
"5-hydroxytryptamine1" should read --5-hydroxytryptamine1--.

COLUMN 16, LINE 24:
"5-hydroxytryptamine1" should read --5-hydroxytryptamine1--.

Signed and Sealed this
Twelfth Day of August, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,673,360 B2 | Page 1 of 1 |
| APPLICATION NO. | : 11/660131 | |
| DATED | : March 18, 2014 | |
| INVENTOR(S) | : Nagata et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1247 days.

Signed and Sealed this
Eleventh Day of August, 2015

Michelle K. Lee
*Director of the United States Patent and Trademark Office*